(12) United States Patent
Taniguchi et al.

(10) Patent No.: US 8,389,246 B2
(45) Date of Patent: Mar. 5, 2013

(54) METHOD FOR NUCLEIC ACID QUANTITATION

(75) Inventors: Kiyomi Taniguchi, Kunitachi (JP); Hideki Kambara, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 82 days.

(21) Appl. No.: 12/292,800

(22) Filed: Nov. 26, 2008

(65) Prior Publication Data

US 2009/0142767 A1 Jun. 4, 2009

(30) Foreign Application Priority Data

Nov. 29, 2007 (JP) ................. 2007-309089

(51) Int. Cl.
*C12P 19/34* (2006.01)
(52) U.S. Cl. ...................................... 435/91.2
(58) Field of Classification Search .............. 435/6, 91.2
See application file for complete search history.

(56) References Cited

U.S. PATENT DOCUMENTS

| 6,210,891 B1 * | 4/2001 | Nyren et al. ............ 435/6 |
| 2003/0124544 A1 * | 7/2003 | Kambara et al. ............ 435/6 |
| 2003/0186314 A1 * | 10/2003 | Kambara et al. ............ 435/6 |

FOREIGN PATENT DOCUMENTS

| EP | 0332 435 | * | 9/1989 |
| JP | 2004-33160 | | 7/2002 |
| JP | 2005-287447 | | 10/2005 |
| WO | WO 9323562 | * | 11/1993 |

OTHER PUBLICATIONS

Zho et al., Nucleic acids Research, vol. 33, No. 15, p. e133 1-11.*
Becker-Andre et al., Nucleic Acids Research, vol. 17, No. 22, pp. 9437-9446, 1989.*
Higuchi, Russell, et al., "Simultaneous Amplification and Detection of Specific DNA Sequences", Research, Bio/Technology, vol. 10, Apr. 1992, pp. 413-417.
Guo-hua Zhou et al., "Quantitative detection of single nucleotide polymorphisms for a pooled sample by a bioluminometric assay coupled with modified primer extension reactions (BAMPER)", Nucleic Acids Research, vol. 29, No. 19e93, (2001), pp. 1-11.

* cited by examiner

*Primary Examiner* — Gary Benzion
*Assistant Examiner* — Cynthia Wilder
(74) *Attorney, Agent, or Firm* — Stites & Harbison, PLLC; Juan Carlos A. Marquez, Esq; Stephen J. Weyer, Esq.

(57) ABSTRACT

It is intended to provide a novel convenient approach for DNA quantitative analysis that overcomes the disadvantages of conventional formulations. A standard DNA sample is prepared by introducing a single-base substitution into target DNA, and a predetermined amount thereof is mixed with a target DNA sample. The target and standard DNAs are amplified using the same primers designed to amplify a region comprising the single-base substitution site. To a hybridization product of a probe capable of binding to a site immediately before the single-base substitution site, ddATP, ddGTP, ddCTP, and ddTTP are sequentially added one by one to perform a complementary strand synthesis reaction. Luciferase reaction-induced luminescence derived from the formed pyrophosphoric acid is detected. The target DNA is quantitated from the amount of the detected luminescence and the amount of the added standard DNA sample.

7 Claims, 6 Drawing Sheets

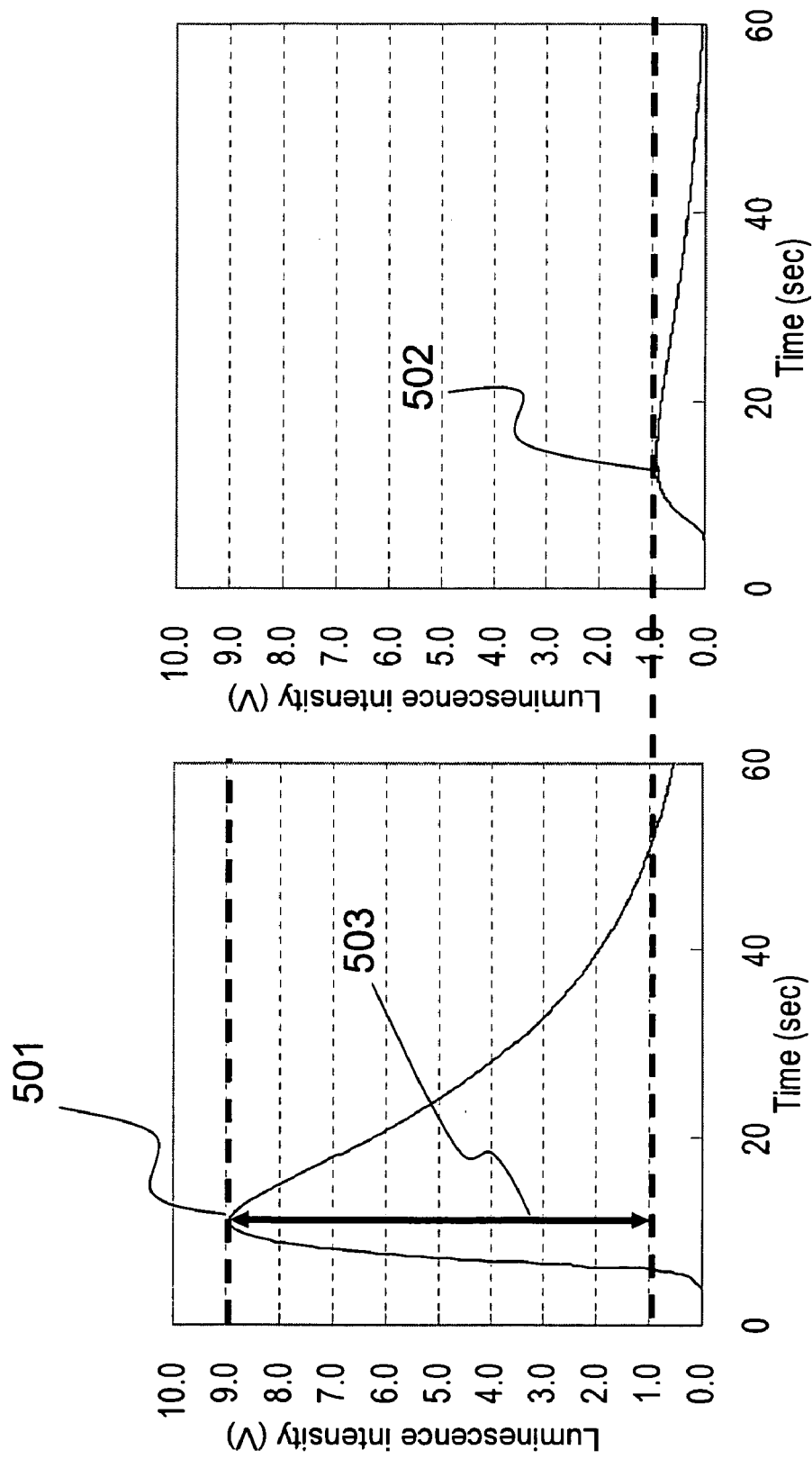

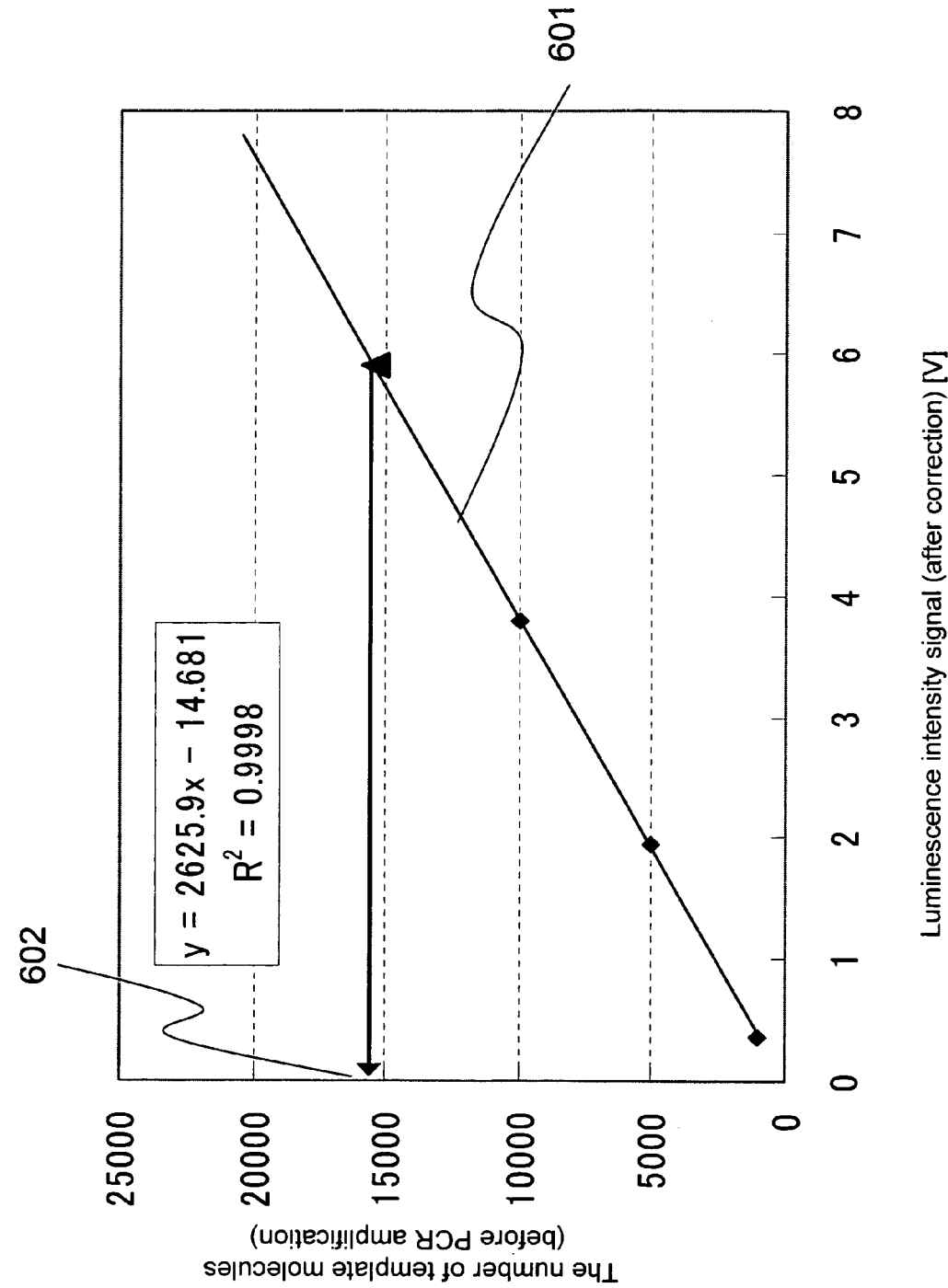

US 8,389,246 B2

METHOD FOR NUCLEIC ACID QUANTITATION

CLAIM OF PRIORITY

The present application claims priority from Japanese patent application JP 2007-309089 filed on Nov. 29, 2007, the content of which is hereby incorporated by reference into this application.

BACKGROUND OF THE INVENTION

1. Field of the Invention

The present invention relates to a method for DNA or RNA quantitative analysis.

2. Background Art

The study of gene expression levels is important for drug development and the study of disease causation. However, in the biological field centered on DNA, target DNAs are often found in small copy numbers in general and are therefore amplified for measurement. However, it is increasingly demanded to accurately determine the copy numbers.

Examples of typical methods for DNA quantitation used currently include three methods, 1) electrophoresis, 2) DNA microarray (JP Patent Publication (Kokai) No. 2004-33160A (2004)), and 3) real-time PCR (Higuchi R, et al, Bio. Technology, 10: 413-417, (1992)). Of them, the electrophoresis is a quantitative method which involves electrophoresing negatively charged DNA, staining bands of separated standard and target samples, and examining the intensity ratio between them. This method requires low analysis cost but disadvantageously has low quantitative accuracy.

The DNA microarray is a quantitative method which involves competitively hybridizing target and standard samples labeled with different phosphors to a DNA chip on which oligonucleotides or cDNAs having complementary sequences thereto are immobilized, and examining a fluorescence intensity ratio. This method is capable of quantitating genes as many as several tens of thousands at a time. However, the obtained fluorescence intensity ratio is susceptible to the influences of the secondary structures of gene sequences and cross hybridization. Thus, this method disadvantageously has poor quantitative accuracy and requires huge analysis (apparatus/DNA chip/reagent) cost.

On the other hand, the real-time PCR is a quantitative method which involves simultaneously amplifying target and standard samples by PCR, while observing fluorescence emitted from the samples, and determining the original amount of the target sample from the number of PCR cycle at which the PCR product reaches a predetermined amount. To examine the amount of the PCR product, an intercalator method using SYBR GREEN or a so-called TaqMan probe method using a gene-specific probe is used. This TaqMan probe is a DNA probe comprising a quencher and a fluorophore linked via the DNA probe. The original TaqMan probe itself does not emit fluorescence. However, the probe is partially degraded during PCR amplification, and the fluorophore released therefrom emits fluorescence. This method has relatively high quantitative accuracy and a detection limit as low as approximately a few molecules. However, this method presents the problems that: it requires an expensive apparatus for monitoring PCR amplification processes in real time; dilution series (at least five different concentrations) of a standard sample having the same sequences must be prepared prior to analysis and analyzed in real time simultaneously with a target sample every time; and it requires complicated procedures and much time and labor.

SUMMARY OF THE INVENTION

An object of the present invention is to provide a novel convenient method for DNA quantitation that overcomes the disadvantages of conventional methods for DNA quantitation.

To attain the object, in the present invention, a portion of target DNA to be quantitated is amplified using a primer having a single-base mismatch (single-base substitution) in proximity to the 3' end to prepare a "standard DNA sample" having a sequence differing by only one base from the target DNA. The standard DNA can be obtained by introducing a single-base mismatch into at least a portion (e.g., a region to be analyzed) of the target DNA.

A predetermined amount of the prepared standard DNA sample is mixed with a target DNA sample. This mixed DNA sample is amplified by PCR and then subjected to quantitative analysis. PCR primers used in this amplification are designed to amplify a region comprising the single-base substitution portion introduced during the preparation of the standard sample. The sequences of regions amplified by PCR are completely the same sequences except for the artificially introduced single-base substitution portions. The target and standard DNAs can be amplified simultaneously, with their ratio maintained.

The obtained amplification product is dissociated into single strands. Then, the abundance ratio among the bases in the single-base substitution portions is measured. The amount of the target DNA is determined from the amount of the added standard DNA sample and this abundance ratio. The abundance ratio in the single-base substitution portions is measured by: performing a complementary strand synthesis reaction using terminator ddNTPs; converting the by-product pyrophosphoric acid formed through this reaction to ATP; and detecting luminescence generated by luciferase reacted with the substrate ATP. A probe used in the complementary strand synthesis reaction is designed such that the 3' end thereof is capable of binding to a site immediately before the substitution portion. Specifically, a template for the nucleic acid substrate incorporated first is a base species in the single-base substitution portion.

Four nucleic acid substrates, ddATP, ddCTP, ddGTP, and ddTTP, used in complementary strand synthesis are added to the reaction vessel in order, and luminescence is observed. Each ddNTP is measured in advance for its luminescence intensity for a predetermined amount of the template to determine a luminescence intensity ratio among the bases. As a result, the abundance ratio among the bases in the substitution portions (i.e., the abundance ratio between the standard and target DNAs) is determined by comparing luminescence intensity among the nucleic acid substrates. Based on this abundance ratio, the target DNA can be quantitated from the amount of the standard DNA sample.

Specifically, the present invention relates to a method for nucleic acid quantitation, comprising the following steps: 1) mixing a target DNA sample with a predetermined amount of a standard DNA sample having a single-base substitution introduced in at least a portion of the target DNA; 2) amplifying the mixed sample using primers designed to amplify a region comprising the single-base substitution site; 3) dissociating the amplified sample into single strands, hybridizing thereto a probe capable of binding to a site immediately before the single-base substitution site, and sequentially adding ddATP, ddGTP, ddCTP, and ddTTP one by one to the hybridization product to perform a complementary strand synthesis reaction; 4) detecting luciferase reaction-induced luminescence derived from pyrophosphoric acid formed through the complementary strand synthesis reaction; and 5) quantitating the target DNA from the amount of the detected luminescence and the amount of the standard DNA sample.

In a certain embodiment, the steps 1) to 5) are performed on plural standard DNA samples differing in the substituted base. In another embodiment, the steps 1) to 5) are performed on plural standard DNA samples differing in concentration.

In the method of the present invention, at least one of the primers used in PCR amplification is biotinylated in advance. As a result, the amplification product can be purified using streptavidin-conjugated beads.

The target DNA sample that can be used may be, for example, a cDNA sample reverse-transcribed from mRNA. An anchor sequence is added in advance to the target DNA. As a result, the standard DNA sample can be prepared using primers, at least one of which has the single-base substitution introduced in this anchor sequence.

In the method of the present invention, the target and standard DNAs may be in a free form. Alternatively, one of them may be immobilized on a solid phase surface. For example, the target DNA sample is immobilized on magnetic beads. As a result, purification or reuse thereof can be performed easily.

In the present invention, a standard DNA sample can be prepared easily by PCR amplification using a portion of a target DNA sample. A luminescence reaction based on a luciferase reaction is used in quantitative analysis. Unlike dNTPs (particularly, dATP), ddNTPs used in complementary strand synthesis do not serve as a substrate for the luciferase reaction, resulting in no background luminescence. Moreover, two or more of the bases are not incorporated as a nucleic acid substrate. Therefore, precise measurement can be achieved, Furthermore, the amount of luminescence is linear-proportional to the amount of DNA. Therefore, quantitation can be achieved with high accuracy. Moreover, PCR amplification and luminescence reaction measurement can be performed independently. Therefore, in the present invention, a trace amount of sample DNA can be amplified by PCR to a large amount and then analyzed efficiently. The present invention requires only a few minutes from the addition of ddNTPs to the completion of measurement and can achieve quantitative analysis in a much shorter time than that required for real-time PCR. As described later, plural standard DNA samples differing in concentration are prepared. As a result, more precise quantitation can be achieved. The present invention can use, in luminescence measurement, a modification of an inexpensive luminometer or an inexpensive photodetector equipped with a photodiode and does not require expensive reagents such as fluorescent probes. As a result, inexpensive quantitative analysis as a whole can be achieved.

Specifically, the present invention can achieve all of (i) high quantitative accuracy, (ii) low analysis apparatus cost, (iii) low reagent cost, and (iv) simple analysis procedures, which are hardly achieved by conventional methods.

BRIEF DESCRIPTION OF THE DRAWINGS

FIG. 5 shows the calculation of a luminescence intensity signal.
FIG. 6 shows the calculation of a luminescence intensity ratio (three standard DNAs are used).

Figure 1:
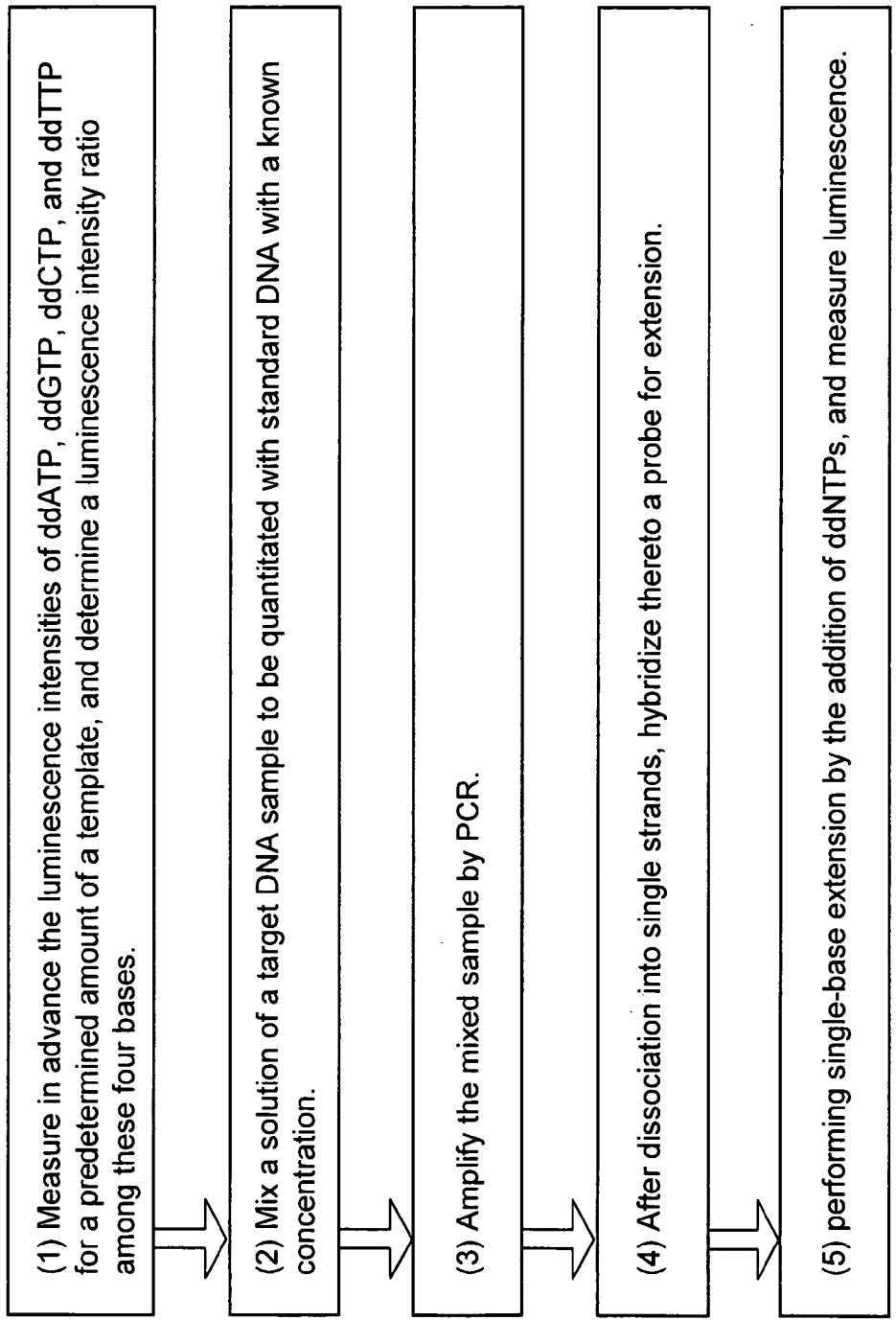
FIG. 1 shows basic procedures of a method of the present invention.

DESCRIPTION OF SYMBOLS 201 mRNA
202 cDNA
203 DNA amplification region to be analyzed
204 priming site of reverse primer
205 priming site of forward primer
301 target DNA sample
302 standard DNA (A)
303 standard DNA (B)
304 standard DNA (C)
305 mixed sample
306 forward primer E
307 5'-biotinylated reverse primer F
401 target DNA sample dissociated into single strand after PCR amplification
402 standard DNA (A) dissociated into single strand after PCR amplification
403 standard DNA (B) dissociated into single strand after PCR amplification
404 standard DNA (C) dissociated into single strand after PCR amplification
405 probe for single-base extension
501 peak of luminescence intensity obtained by first addition of ddNTP
502 peak of luminescence intensity obtained by second addition of ddNTP
501 luminescence intensity signal
601 calibration curve prepared from three standard DNAs (A), (B), and (C)
602 the number of molecules corresponding to target DNA sample

DETAILED DESCRIPTION OF THE PREFERRED EMBODIMENTS

Basic procedures of an analysis method of the present invention will be outlined below. The method of the present invention is schematically shown in FIG. 1.
(1) Measurement of Luminescence Intensity Ratio Among ddNTPs Each ddNTP (ddATP, ddGTP, ddCTP, and ddTTP) is measured in advance for its luminescence intensity for a predetermined amount of a target DNA sample to determine a luminescence intensity ratio among these four bases.
(2) Mixing Target DNA Sample With Standard DNA Sample (Known Concentration)

A standard DNA sample is prepared as follows: first, a primer set for preparing standard DNA is prepared. The primers are hybridized to the 5' and 3' sides of the target DNA, respectively. A region flanked by these primers is an amplification region. At least one of the primers is designed such that the primer sequence has a base (substituted base) different from that in the target DNA, at the 3rd to 10th base position from the 3' end and has at least 16 or more bases in the 5' sequence from this substituted base. A portion of the target DNA sample is collected and amplified by PCR using the primers to prepare a standard DNA sample. The standard DNA sample is purified as a single strand and then quantitated from absorbance. A predetermined amount of the quantitated standard DNA sample is mixed with the target DNA.

(3) PCR Amplification

The mixed sample of the target and standard DNAs is simultaneously amplified by PCR using a primer free from the 3'-side sequence from the substituted base (i.e., a primer which is shorter than that used in the preparation of the standard DNA sample and is free from the substituted base portion). The target and standard DNAs have the same sequences in the regions to be amplified except for the substituted base portion and therefore have the same PCR amplification rates.

(4) Hybridization Of Probe For Extension

The amplification product of the target and standard DNAs is purified and then dissociated into single strands. A probe for extension and DNA polymerase are added thereto. When the PCR primers for amplification might remain, the 3' ends which are likely to contribute to complementary strand synthesis are blocked by the addition of DNA polymerase and ddNTPs, followed by repurification.

(5) Single-Base Extension And Luminescence Measurement

Four ddNTPs are sequentially added to the hybridization product to perform single-base extension. Luminescence induced by a luciferase reaction is measured. The probe for extension is designed to hybridize to the 3'-side sequence adjacent to the single-base substitution portion. As a result, the type of the nucleic acid substrate ddNTP incorporated through the single-base extension reaction differs in the single-base substitution portion. The single-base extension occurs, during which the ddNTP is incorporated to form pyrophosphoric acid. This pyrophosphoric acid is converted to ATP, which in turn brings about luminescence through a luciferase reaction. Specifically, the obtained luminescence intensity is proportional to the amount of the formed pyrophosphoric acid. The type of the incorporated base species differs between the target and standard DNAs. Therefore, the target DNA can be quantitated from the ratio of the amount of luminescence and the amount of the added standard DNA sample.

Hereinafter, the present invention will be described specifically with reference to Examples. However, the present invention is not intended to be limited to these Examples.

Example 1

Example 1 shows the quantitation of an expression level of EFF1G gene in human colon cancer cells (HCT116).

Figure 2:
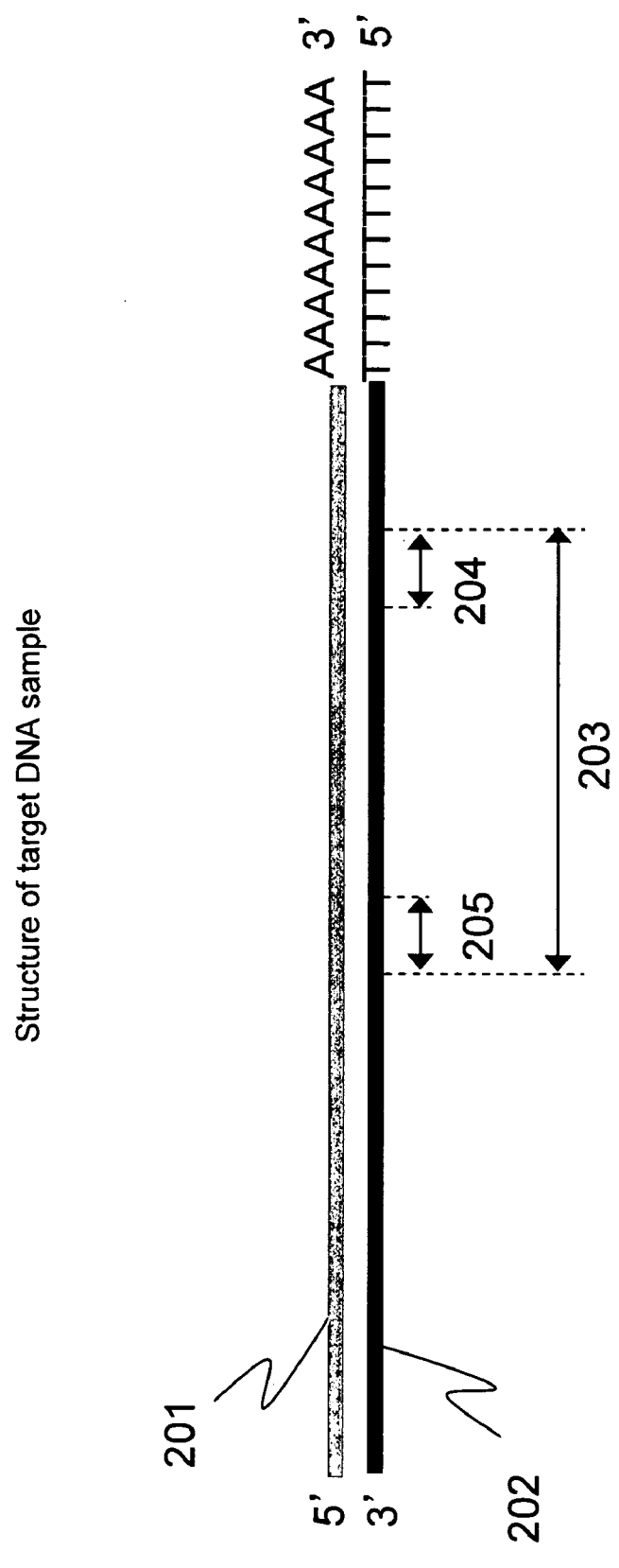
FIG. 2 shows the structure of a target DNA sample.
Figure 3:
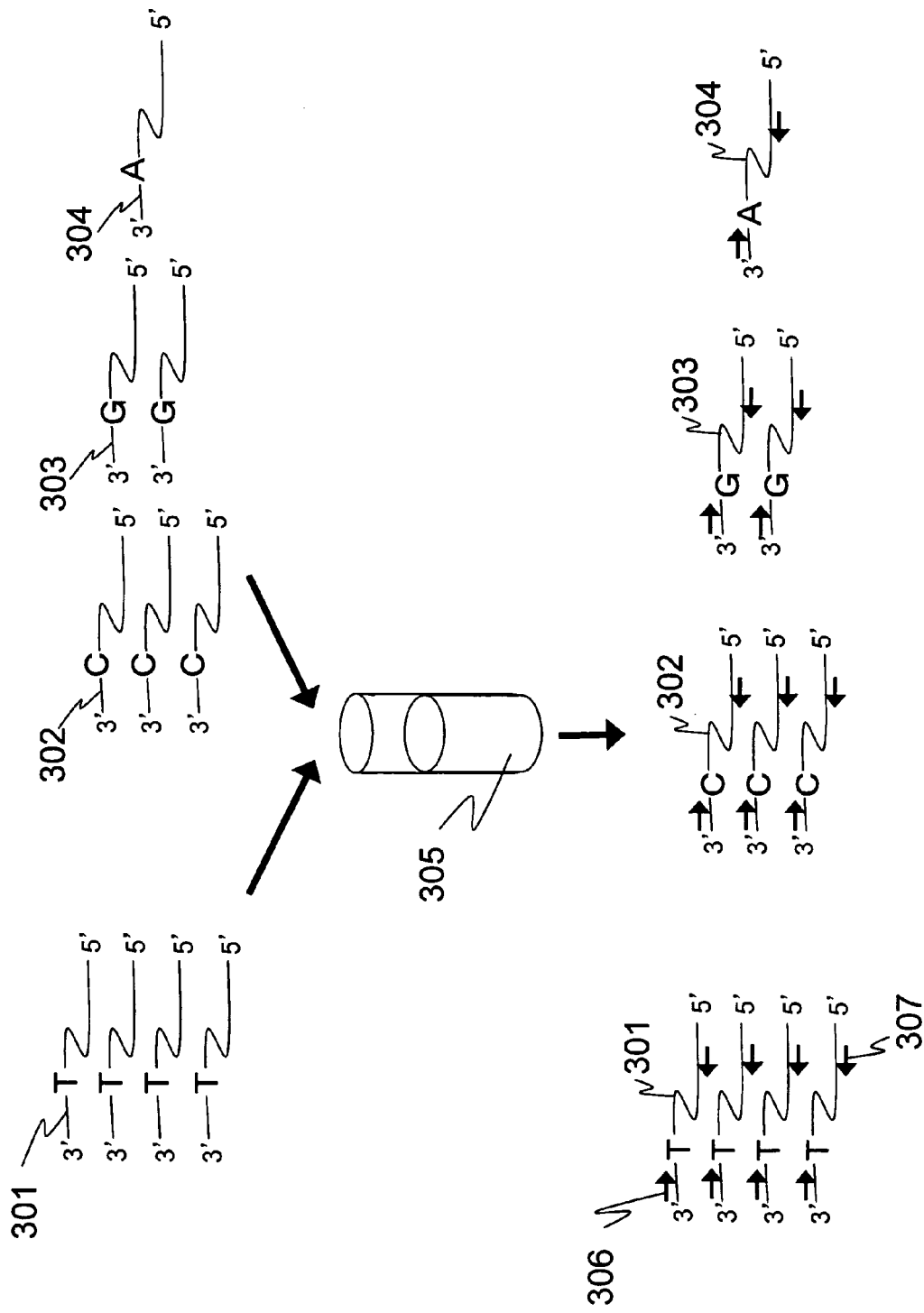
FIG. 3 shows the mixing of the target DNA sample with a standard DNA sample and PCR amplification.

Full-length cDNA (202) containing a target region was prepared from human colon cancer mRNA (201) according to Step 1 described below. This long cDNA contains a DNA sequence region (203) to be analyzed as a target for quantitative analysis. The target sequence is represented by SEQ ID NO: 1 shown in Sequence Listing. This sequence comprises a priming site of a reverse primer (204), the amplification region to be analyzed (203), and a priming site of a forward primer (205), as schematically shown in FIG. 2.

A portion of the cDNA sample was collected, and a single-stranded DNA fragment having the same sequence as that of the target except for a single-base substitution portion was prepared according to Step 2. In the present Example, the forward primer was designed such that its sequence contained a substitution portion at the 7th base position from the 3' end. Of course, the present invention is not limited to this example. In Example 1 shown here, three standard DNA fragments containing different single-base substitutions were prepared for target DNA and added in different amounts to the target. The closer the amounts of the target and standard DNA samples are to each other, the higher quantitative accuracy becomes. Thus, the standard DNA samples are added at three different concentrations, one of which is close to the amount of the target. As a result, more accurate quantitative analysis can be achieved.

Predetermined amounts of the standard DNA samples thus prepared are added to the target DNA sample. The mixed sample is amplified by PCR according to Step 3. PCR primer sequences are common to all the samples. The target and standard DNA samples differ in the amplification regions by only one base and can therefore be amplified at almost the same rates. A primer used in this PCR amplification is located on the terminal side (5' side) from the single-base substitution portion introduced in the standard DNA samples. Therefore, the primer sequence is free from the substitution site. After amplification, single-stranded DNAs are obtained by purification. The copy numbers of the target DNA and the predetermined amounts of the standard DNA samples are amplified by this PCR, with their original abundance ratios maintained.

The obtained DNA samples, DNA polymerase, an enzyme for converting pyrophosphoric acid to ATP (ATP sulfurylase or PPDK), luciferase, and substrates for these enzyme reactions are placed together with a buffer solution in a reaction cell and well stirred. Nucleic acid substrate ddNTPs are sequentially added thereto. The obtained luminescence intensity is measured. A calibration curve is obtained by plotting the amounts of the standard DNA samples as the ordinate and their luminescence intensities as the abscissa. The amount of the target DNA can be determined from this graph and luminescence intensity obtained from single-base complementary strand synthesis using the target DNA as a template (FIG. 6). The nucleic acid substrate ddNTPs may contain ATP or pyrophosphoric acid, which sometimes brings about a luminescence signal even without complementary strand synthesis. To eliminate these influences, background luminescence is measured by the addition of ddNTPs again after measurement. The amount of luminescence is defined as a value obtained by subtracting this background. As a result, accurate results are obtained.

Step 1: Preparation Of Target DNA Sample

From approximately $10^6$ human colon cancer cells (HCT116), total RNA (approximately 400 ng/μL, 25 μL, 10 μg in total) was extracted and purified using RNeasy Midi Kit (QIAGEN). To a PCR tube placed on ice, 2.5 μL of the total RNA (approximately 1 μg), 1 μL of 50 μM oligo(dT)$_{20}$ primer, 1 μL of dNTP Mix (10 mM each), and 8.5 μL of sterilized water were added and mixed. The mixture was heated at 65° C. for 5 minutes using a thermal cycler (ABI) to disrupt the higher order structure of the RNA for hybridization of the oligo(dT)$_{20}$ primer. The same PCR tube was placed again on ice, and 4 μL of 5× First Strand Buffer (250 mM Tris-HCl (pH 8.3), 375 mM KCl, 15 mM MgCl$_2$), 1 μL of DTT (0.1 M), 1 μL of RNase OUT (40 units/μL, Invitrogen Corp.), and 1 μL of Super Script III (200 units/μL, Invitrogen Corp.) were added thereto and mixed. This mixture was heated at 50° C. for 50 minutes using a thermal cycler to perform a reverse-transcription reaction. Subsequently, the mixture was heated at 70° C. for 15 minutes for inactivation of the reverse transcriptase. 1 μL of RNase H (2 units/μL) was added thereto, and the mixture was heated at 37° C. for 20 minutes using a thermal cycler to separate single-stranded cDNA from the mRNA. As a result, 21 μL of single-stranded cDNA was obtained from the total RNA (1 μg) derived from human colon cancer cells. A 1 μL aliquot of this cDNA was further diluted $5\times10^3$ folds with sterilized water to prepare a target DNA sample (5 mL) (cDNA derived from 10 pg of the total RNA/μL).

Step 2: Preparation Of Standard DNA (Single-Stranded)

Three 5'-biotinylated forward primers A (SEQ ID NO: 2), B (SEQ ID NO: 3), and C (SEQ ID NO: 4) having a substituted base species different from that in the target sequence as a template, at the 7th base position from the 3' end, and a reverse primer D (SEQ ID NO: 5) were prepared. First, three PCR tubes (tubes A, B, and C) were placed on ice. To each of the tubes, 29 μL of sterilized water, 10 μL of ×10 PCR Buffer, 10 μL of dNTP Mix (2.5 mM each), 20 μL of ×5 Q-solution, 10 μL of the reverse primer D (10 μM) (SEQ ID NO: 5), 1 μL of Taq DNA polymerase (5 units/μL, QIAGEN), and 10 μL of the target DNA sample were added. Further, 10 μL of the 5'-biotinylated forward primer A (10 μM) was added to the tube A, 10 μL of the 5'-biotinylated forward primer B (10 μM) was added to the tube B, and 10 μL of the 5'-biotinylated forward primer C (10 μM) was added to the tube C. Each tube was well mixed. These mixtures were heated at 94° C. for 1 minute→50 cycles of 94° C. for 30 seconds, 58° C. for 30 seconds, and 72° C. for 1 minute→72° C. for 7 minutes for PCR amplification using a thermal cycler to obtain three double-stranded PCR products A, B, and C. Subsequently, to remove the dNTPs and PCR primers remaining in the sample, each PCR product was purified (50 μL) using QIAquick PCR Purification Kit (QIAGEN). Each DNA concentration was measured using an absorption spectrometer to confirm that all the concentrations were approximately 1 μg/μL.

These PCR products A, B, and C were separately diluted to 200 μL by the addition of 150 μL of 1× Binding & Washing Buffer (5 mM Tris-HCl (pH 7.5), 0.5 mM EDTA, 1 M NaCl). 600 μL of streptavidin-coated magnetic beads (1 μm in diameter, $10^7$ pieces/μL, DYNAL BIOTECH) was collected into a 1.5-mL tube and captured by placing a magnet in proximity to the tube, and the supernatant was removed. The magnetic beads were washed three times with 600 μL of Binding & Washing Buffer and then suspended in 600 μL of this buffer. A 200 μL aliquot of this magnetic bead suspension was added to each PCR product sample and well stirred for 60 minutes using a rotor (600 rpm, room temperature) to bind the PCR product onto the magnetic bead surface via the streptavidin-biotin bond. To remove excessive PCR products unbound with the magnetic beads, the magnetic beads were captured with a magnet, and the supernatant was removed. The beads were washed twice with 200 μL of Binding & Washing Buffer. Subsequently, the magnetic beads bound with each PCR product were suspended in 300 μL of 0.1 N NaOH and left standing at room temperature for 5 minutes. The magnetic beads were captured with a magnet, and each supernatant was collected into a new tube. To this supernatant, 60 μL of 1 M Tris (pH 7.5) and 300 μL of 0.1% Tween (pH 7.5) were added for neutralization. To each sample, 1 mL of phenol:chloroform:isoamyl alcohol (25:24:1, v/v, Invitrogen Corp.) was added. After vortex for 3 minutes, the mixture was centrifuged (15000 rpm, 5 minutes, room temperature) (phenol/chloroform purification). The upper layer of each centrifuged solution was collected (approximately 650 μL) into a new tube and purified and concentrated (approximately 250 μL) using QIAquick PCR Purification Kit. To these samples, 25 μL of sodium acetate (3 M) and 625 μL of ethanol (99.5%, −30° C.) were added, and the mixture was frozen at −80° C. for 15 minutes and then centrifuged (15000 rpm, 15 minutes, 4° C.). 180 μL of ethanol (70%, −30° C.) was added to each sample. The mixture was centrifuged (15000 rpm, 5 minutes, 4° C.), and the supernatant was removed (ethanol precipitation purification). Each pellet was dried and then suspended in 10 μL of sterilized water. Each DNA concentration was measured using an absorption spectrometer to confirm that all the concentrations were approximately 2 μg/μL (approximately $2\times10^{12}$ molecules/μL). These suspensions were diluted with sterilized water to prepare 1 mL each of approximately 1000 molecules/μL standard DNA (A) (SEQ ID NO: 6), approximately 500 molecules/μL standard DNA (B) (SEQ ID NO: 7), and approximately 100 molecules/μL standard DNA (C) (SEQ ID NO: 8). These standard DNAs are single-stranded DNAs having only one substituted base relative to the target DNA.

Step 3: Mixing Of Target DNA sample with standard DNA Sample and PCR Amplification To a tube placed on ice, 10 μL of the target DNA sample (301) having a sequence free from the single-base substitution and 10 μL each of the standard DNAs (A) (302), (B) (303), and (C) (304) were added to prepare a mixed sample (305). This mixed sample was mixed with 116 μL of sterilized water, 40 μL of ×10 PCR Buffer, 40 μL of dNTP Mix (2.5 mM each), 80 μL of ×5 Q-solution, 40 μL of a forward primer E (SEQ ID NO: 9) (10 μM) (306), 40 μL of a 5'-biotinylated reverse primer F (10 μM) (SEQ ID NO: 5) (307), and 4 μL of Taq DNA polymerase (5 units/μL, QIAGEN). This mixture was heated at 94° C. for 1 minute→50 cycles of 94° C. for 30 seconds, 58° C. for 30 seconds, and 72° C. for 1 minute→72° C. for 7 minutes for PCR amplification using a thermal cycler. The primer used in this PCR amplification is located on the terminal side from the single-base substitution site artificially introduced in the standard DNAs (A), (B), and (C). Therefore, the four templates present in the mixed sample are amplified with the same efficiency. Specifically, the ratio among the four templates in the sample after PCR amplification is kept the same as that before amplification. To remove the dNTPs and PCR primers remaining in 400 μL of the PCR product, the PCR product was purified (500 μL) using QIAquick PCR Purification Kit. Each DNA concentration was measured using an absorption spectrometer to confirm that the concentrations were approximately 100 ng/μL.

Step 4: Dissociation Into Single Strands

To the obtained PCR product, 500 μL of 1× Binding & Washing Buffer was added. 500 μL of streptavidin-coated magnetic beads was collected into a 1.5-mL tube and captured by placing a magnet in proximity to the tube, and the supernatant was removed. The magnetic beads were washed three times with 500 μL of Binding & Washing Buffer and then suspended in 500 μL of this buffer. A 500 μL aliquot of this magnetic bead suspension was added to the PCR product and well stirred for 60 minutes using a rotor (600 rpm, room temperature) to bind the PCR product onto the magnetic bead surface via the streptavidin-biotin bond. To remove excessive PCR products unbound with the magnetic beads, the magnetic beads were captured with a magnet, and the supernatant was removed. The beads were washed twice with 500 μL of Binding & Washing Buffer. Subsequently, the magnetic beads bound with each PCR product were suspended in 450 μL of 0.1 N NaOH and left standing at room temperature for 5 minutes. The magnetic beads were captured with a magnet, and the supernatant was collected into a new tube. To this supernatant, 90 μL of 1 M Tris (pH 7.5) and 450 μL of 0.1% Tween (pH 7.5) were added for neutralization. 1 mL of phenol:chloroform:isoamyl alcohol (25:24:1, v/v.) was further added thereto. After vortex for 3 minutes, the mixture was centrifuged (15000 rpm, 5 minutes, room temperature) (phenol/chloroform purification). The upper layer of the centrifuged solution was collected (approximately 900 μL) into a new tube and purified and concentrated (approximately 250 μL) using QIAquick PCR Purification Kit. To these samples, 25 μL of sodium acetate (3 M) and 625 μL of ethanol (99.5%, −30° C.) were added, and the mixture was frozen at −80° C. for 15 minutes and then centrifuged (15000 rpm, 15 minutes, 4° C.). 180 µL of ethanol (70%, −30° C.) was added thereto. The mixture was centrifuged (15000 rpm, 5 minutes, 4° C.), and the supernatant was removed (ethanol precipitation purification). The pellet was dried and then suspended in 100 µL of sterilized water. Each DNA concentration was measured using an absorption spectrometer to confirm that the concentrations were approximately 150 ng/µL (approximately $5 \times 10^{11}$ molecules/µL).

Figure 4:
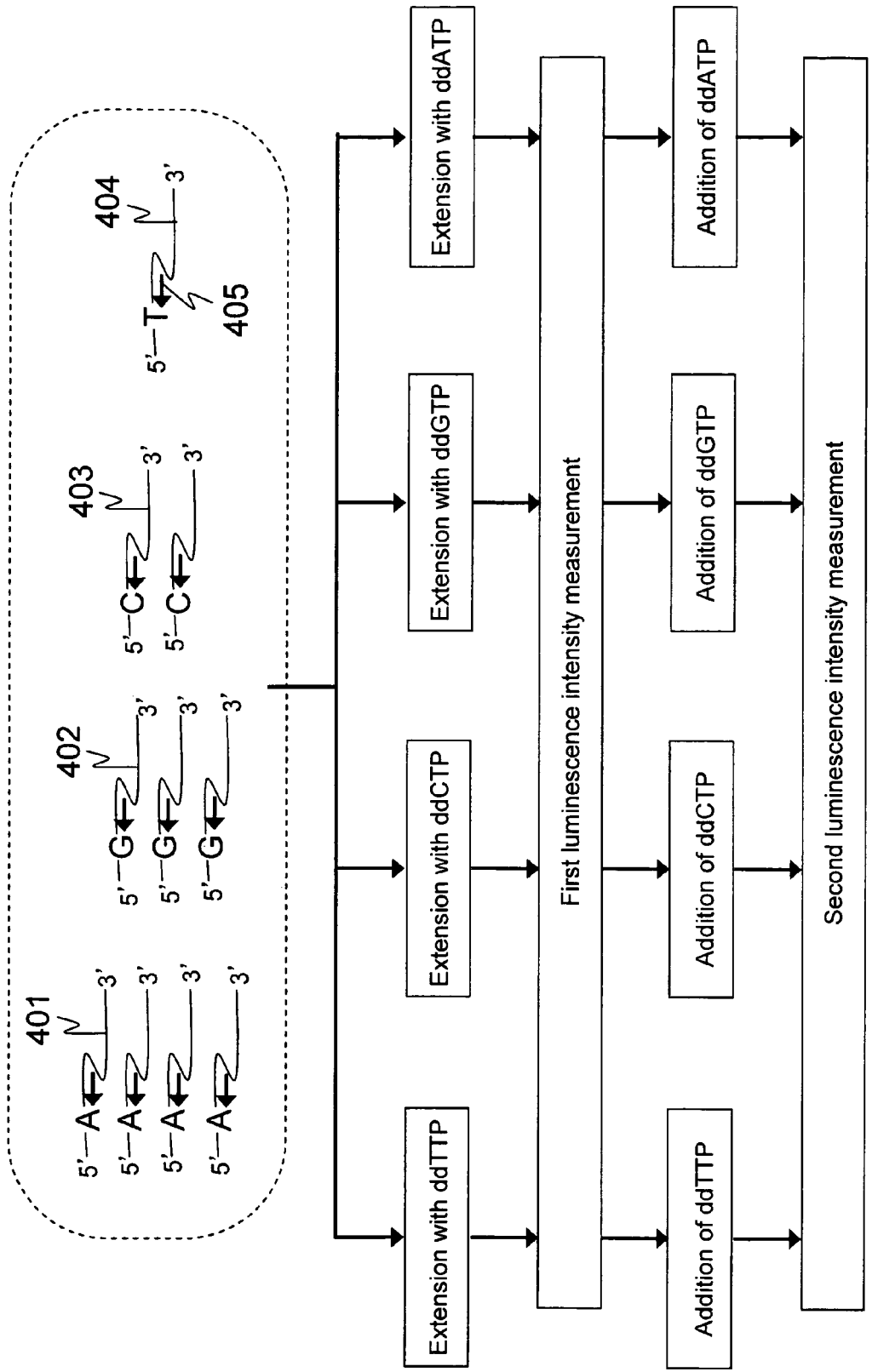
FIG. 4 shows single-base extension and luminescence intensity measurement.

Step 5: Measurement of Chemical Luminescence Attributed to Single-Base Extension 8 µl of the single-stranded PCR amplification product (401, 402, 403, and 404) was mixed with 3 µl of a probe for single-base extension (50 µM, SEQ ID NO: 10) (405), 3 µl of 10× Hybridization Buffer (100 mM Tris-acetate, 20 mM Mg-Acetate, pH 7.75), and 16 µl of sterilized water. The mixed solution was heated at 92° C. for 30 seconds and 50° C. for 3 minutes using a thermal cycler and cooled to 4° C. A 4 µL aliquot of this solution was mixed with 120 µL of a luminescence reagent (0.065 U/µL Sequenase, 100 mM Tricine, 2 mM EDTA, 20 mM Mg-Acetate, 33.8 U/ml PPDK-E, 523.0 GLU/ml Luciferase (LUC-H), Apyrase 1.5 U/ml Grade VI, 0.4 mM Luciferin, 0.04 mM PEP, 0.2 mM AMP, 0.10% BSA, 2 mM DTT, pH 7.75) and incubated at 30° C. for 1 minute. A 30 µL aliquot thereof was dispensed to each of four connected tubes, to which 0.5 µL each of ddNTPs (100 µM each) whose PPi was degraded in advance with PPase was added to perform luminescence detection (measurement time: 1 minute). Next the same amounts of ddNTPs were added thereto to perform luminescence detection again (measurement time: 1 minute) (FIG. 4).

FIG. 5 shows changes over time in the luminescence intensity thus obtained. In this context, the ordinate of the graph represents luminescence intensity (V), and the abscissa thereof represents elapsed time. As shown in FIG. 5, two luminescence intensity peaks 501 and 502 appear along with two additions of ddNTPs. The peak 501 appears by the first addition of ddNTPs, and the peak 502 appears by the second addition of ddNTPs. The second peak 502 corresponds to background luminescence. Therefore, a luminescence intensity signal is defined as 503 obtained by subtracting the peak 502 from the peak 501.

The luminescence intensity signal was measured on 1 µL ($2 \times 10^{10}$ molecules) each of the four standard DNAs mixed with 30 µL of the luminescence reagent. An extension intensity ratio was obtained from the luminescence intensity signals of these four standard DNAs relative to the signal value derived from ddATP (the middle line of Table 1). The difference in the degree of extension among the types of base species was corrected by dividing the luminescence intensity signal values by these numeric values of the extension intensity ratio. The upper line of Table 1 shows the luminescence signal values before correction, and the lower line of Table 1 shows the luminescence signal values after correction. The corrected signal values were used to prepare a calibration curve 601 shown in FIG. 6 for quantitating the number of molecules of the target DNA sample. The luminescence intensity signal values (after correction) are plotted in the abscissa of the graph, and the numbers of molecules of the standard DNAs before PCR amplification are plotted in the ordinate thereof. Next, the calibration curve 601 was used to obtain the number of molecules (15500) corresponding to the target DNA sample as shown in an arrow 602, from the luminescence intensity signal value (after correction) obtained from the target DNA sample. This value is almost equal to the known number of molecules (15000) of the target, demonstrating that quantitation with sufficient accuracy can be achieved.

TABLE 1

Correction of luminescence intensity signal

| | Type of ddNTP | | | |
|---|---|---|---|---|
| | ddTTP | ddCTP | ddGTP | ddATP |
| Luminescence intensity signal | 7.32 | 4.22 | 2.00 | 0.37 |
| Extension intensity ratio | 1.24 | 1.11 | 1.03 | 1.0 |
| Luminescence intensity signal (after correction) | 5.90 | 3.80 | 1.94 | 0.37 |

Table 2 shows results of quantitating the number of molecules of the target DNA sample when only one standard DNA is mixed therewith. The upper line of Table 2 shows the number of molecules (before PCR amplification) of the standard DNA added to the target DNA sample. The middle line thereof shows the luminescence intensity signal ratio of the target DNA sample to each standard DNA in the mixed sample. The lower line thereof shows the number of molecules of the target DNA sample estimated therefrom (15500, 15200, and 15900, respectively). In this case as well, the number of molecules of the target DNA sample is approximately 15000, demonstrating favorable quantitative accuracy can be obtained.

TABLE 2

Calculation of luminescence intensity ratio

| | Type of standard DNA | | |
|---|---|---|---|
| | Standard DNA (A) | Standard DNA (B) | Standard DNA (C) |
| The number of molecules of standard DNA before PCR amplification | 10000 | 5000 | 1000 |
| Luminescence intensity ratio of mixed sample | 1.55 | 3.04 | 15.9 |
| Quantitated value (the number of molecules) | 15500 | 15200 | 15900 |

Example 2

Example 2 shows the quantitation of a target DNA sample obtained by reverse transcription of mRNA on oligo(dT)$_{30}$ magnetic beads.

An expression level of EFF1G gene in human colon cancer cells (HCT116) was quantitated in the same way as in Example 1. In the present Example, RNA prepared from the colon cancer cells according to the Step 1 is a starting material. cDNA was prepared using oligo(dT)$_{30}$-immobilized magnetic beads prepared according to Step 6. The cDNA was prepared according to Step 7. Three standard DNA samples were prepared according to the Step 2. These standard DNA samples were mixed at different proportions with the target DNA sample, and the mixed sample was amplified by PCR using the same primers according to Step 8. This amplification product was dissociated into single strands according to the Step 4 of Example 1. Luminescence attributed to single-base extension was measured according to the Step 5 to perform the quantitative analysis of the target DNA sample.

Step 6: Preparation of Oligo(dT)$_{30}$-Immobilized Magnetic Beads

Magnetic beads (1 µm in diameter, $10^7$ pieces/µL, DYNAL BIOTECH) having the surface coated with streptavidin were well suspended, and 100 μL of the suspension (containing $10^9$ magnetic beads) was collected into a 1.5-mL tube. The magnetic beads were captured by placing a magnet in proximity to the 1.5-mL tube, and the supernatant was removed. The magnetic beads were resuspended in 100 μL of Binding & Washing Buffer and captured with a magnet, and the supernatant was removed to wash the magnetic beads. This washing procedure was repeated three times. On the other hand, 6.67 μL of oligo(dT)$_{30}$ (100 pmol/μL) having the 5' end modified with two biotin molecules and containing a six-carbon spacer sequence adjacent thereto was prepared into 400 μL of a dilute solution of oligo(dT)$_{30}$ (1.67 pmol/μL, containing $4.0 \times 10^{14}$ molecules) by the addition of Binding & Washing Buffer. This 400 μL of the dilute solution of oligo(dT)$_{30}$ was mixed with the washed magnetic beads and well stirred for 60 minutes using a rotor to bind the oligo(dT)$_{30}$ onto the magnetic bead surface via the streptavidin-biotin bond. To remove excessive oligo(dT)$_{30}$ unbound with the magnetic beads, the magnetic beads were captured with a magnet, and the supernatant was removed. The beads were washed twice with Binding & Washing Buffer. To remove RNase, the magnetic beads were washed twice with a solution A (0.1 N NaOH, 0.05 M NaCl, treated with DEPC) and once with a solution B (0.1 M NaCl, treated with DEPC). Then, 100 μL of sterilized water was added to the magnetic beads to prepare a oligo(dT)$_{30}$-immobilized magnetic bead suspension ($1 \times 10^7$ pieces/μL, the estimated number of oligo(dT)$_{30}$ immobilized: approximately $20.0 \times 10^5$ molecules/magnetic bead).

Step 7: Preparation of Single-Stranded cDNA Sample Using Oligo(dT)$_{30}$-Immobilized Magnetic Beads From approximately $10^6$ human colon cancer cells (HCT116), total RNA (approximately 400 ng/μL, 25 μL, 10 μg in total) was extracted and purified using RNeasy Midi Kit (QIAGEN). This total RNA was diluted to a concentration of approximately 100 pg/μL with sterilized water. To a PCR tube placed on ice, 1 μL of the total RNA (approximately 100 ng), 1 μL of the oligo(dT)$_{30}$-immobilized magnetic beads ($1 \times 10^7$ pieces/μL), 1 μL of dNTP Mix (10 mM each), and 20 μL of sterilized water were added and mixed. The mixture was heated at 70° C. for 55 minutes for hybridization of the oligo(dT)$_{30}$ primer on the magnetic beads to the mRNA poly (A) tail using a thermal cycler (ABI). The same PCR tube was placed again on ice, and 6 μL of 5× First Strand Buffer (250 mM Tris-HCl (pH 8.3), 375 mM KCl, 15 mM MgCl$_2$), 1 μL of DTT (0.1 M), 1 μL of RNase OUT (40 units/μL, Invitrogen Corp.), and 1 μL of Super Script III (200 units/μL, Invitrogen Corp.) were added thereto and mixed. This mixture was heated at 50° C. for 50 minutes using a thermal cycler to perform a reverse-transcription reaction. Subsequently, the mixture was heated at 85° C. for 3 minutes for inactivation of the reverse transcriptase. 1 μL of RNase H (2 units/μL) was added thereto, and the mixture was heated at 37° C. for 20 minutes using a thermal cycler to separate single-stranded cDNA from the mRNA. The cDNA-immobilized magnetic beads were captured by placing a magnet in proximity to the PCR tube, and the supernatant containing the remaining reagents was removed. The magnetic beads were washed twice with 50 μL of a washing solution (10 mM Tris, 0.1% Tween 20) and resuspended in 10 μL of this solution. As a result, the target DNA sample (single-stranded cDNA) immobilized on the magnetic bead surface was obtained from the total RNA (100 pg) derived from human colon cancer cells.

Step 8: Mixing of Target DNA Sample with Standard DNA and PCR Amplification

To 10 μL of the target DNA sample thus immobilized on the magnetic beads, 10 μL each of standard DNAs (A) (SEQ ID NO: 6), (B) (SEQ ID NO: 7), and (C) (SEQ ID NO: 8 prepared according to the Step 2 was added to prepare a mixed sample. To this mixed sample, 116 μL of sterilized water, 40 μL of ×10 PCR Buffer, 40 μL of dNTP Mix (2.5 mM each), 80 μL of ×5 Q-solution, 40 μL of a forward primer E (SEQ ID NO: 9) (10 μM), 40 μL of a 5'-biotinylated reverse primer F (10 μM) (SEQ ID NO: 5), and 4 μL of Taq DNA polymerase (5 units/μL, QIAGEN) were added and mixed. This mixture was heated at 94° C. for 1 minute→50 cycles of 94° C. for 30 seconds, 58° C. for 30 seconds, and 72° C. for 1 minute→72° C. for 7 minutes for PCR amplification using a thermal cycler. The primer used in this PCR amplification is designed such that the primer is located on the terminal side from the single-base substitution site contained in the standard DNAs (A), (B), and (C). Therefore, the four templates present in the mixed sample are amplified with the same efficiency. Specifically, the ratio among the four templates in the sample after PCR amplification is kept the same as that before amplification. The supernatant containing the PCR product was collected into another tube by placing a magnet in proximity to the PCR tube. To collect even the PCR product synthesized on the remaining magnetic beads, the magnetic beads were washed with 10 μL of 0.1 N NaOH, and this washing solution was mixed with the supernatant collected beforehand. To remove the dNTPs and PCR primers remaining in 410 μL of this PCR product, the PCR product was purified (500 μL) using QIAquick PCR Purification Kit. Each DNA concentration was measured using an absorption spectrometer to confirm that the concentrations were approximately 100 ng/μL. The sample was dissociated into single strands according to the Step 4. Then, chemical luminescence attributed to single-base extension was measured according to the Step 5 to perform the quantitative analysis of the target DNA sample.

Example 3

Example 3 shows the quantitation of an expression level of EFF1G gene in human colon cancer cells (HCT116) by reusing cDNA immobilized on magnetic beads.

When a target to be analyzed is obtained in the form of single-stranded cDNA immobilized on magnetic beads as shown in Example 2, the immobilized cDNA is used as a template for 2nd-strand cDNA synthesis. After removal of primers, etc., the synthesized complementary strand is released into a solution and may be used as a target for quantitative analysis. Three standard DNAs (Step 2 of Example 1) are added at different proportions to the synthesized complementary strand sample, and this mixed sample is amplified by PCR using the same primers. The primer used in this PCR amplification is designed to hybridize to the terminal side from the single-base substitution site introduced in the standard DNAs. Therefore, the target DNA sample and the standard DNAs have completely the same application efficiency, as in Examples 1 and 2. The amplification product was dissociated into single strands according to the Step 4 of Example 1. Luminescence attributed to single-base extension was measured according to the Step 5 to perform the quantitative analysis of the target DNA sample.

In the present Example, the original cDNA can be allowed to remain on the magnetic beads. Therefore, the sample can advantageously be subjected to quantitative analysis repeatedly, if necessary.

Step 9: 2nd-Strand cDNA Synthesis

First, oligo(dT)$_{30}$-immobilized magnetic beads were prepared according to the Step 6 of Example 2. Next, a single-stranded cDNA sample (cDNA derived from 100 pg of total RNA) was prepared using the oligo(dT)$_{30}$-immobilized magnetic beads according to the Step 7. Subsequently, to 10 μL of a suspension of the single-stranded cDNA immobilized on the magnetic beads, 39 μL of sterilized water, 10 μL of ×10 PCR Buffer, 10 μL of dNTP Mix (2.5 mM each), 20 μL of ×5 Q-solution, 10 μL of a forward primer E (SEQ ID NO: 9) (10 μM), and 1 μL of Taq DNA polymerase (5 units/μL, QIAGEN) were added and mixed. This mixture was heated at 94° C. for 1 minute→94° C. for 30 seconds, 50° C. for 30 seconds, and 72° C. for 3 minutes for 2nd-strand cDNA synthesis using a thermal cycler. The magnetic beads were captured by placing a magnet in proximity to the tube, and the supernatant containing excessive primers unused in the reaction was removed. The magnetic beads were washed twice with 100 μL of a washing solution. The magnetic beads were suspended in 10 μL of sterilized water heated to 95° C. and captured using a magnet, and the supernatant was then collected. This supernatant contains 2nd-strand cDNA. This procedure was performed twice to obtain 20 μL of a solution of 2nd-strand cDNA as a target DNA sample.

Step 10: PCR Amplification of Mixed Solution of 2nd cDNA and Standard DNA

To 20 μL of the 2nd-strand cDNA, 10 μL each of standard DNAs (A) (SEQ ID NO: 6), (B) (SEQ ID NO: 7), and (C) (SEQ ID NO: 8) prepared according to the Step 2 was added to prepare a mixed sample. To 50 μL of this mixed sample, 106 μL of sterilized water, 40 μL of ×10 PCR Buffer, 40 μL of dNTP Mix (2.5 mM each), 80 μL of ×5 Q-solution, 40 μL of a forward primer E (SEQ ID NO: 9) (10 μM), 40 μL of a 5'-biotinylated reverse primer F (10 μM) (SEQ ID NO: 5), and 4 μL of Taq DNA polymerase (5 units/μL, QIAGEN) were added and mixed. This mixture was heated at 94° C. for 1 minute→50 cycles of 94° C. for 30 seconds, 58° C. for 30 seconds, and 72° C. for 1 minute→72° C. for 7 minutes for PCR amplification using a thermal cycler. The primer used in this PCR amplification is designed to hybridize to the terminal side from the single-base substitution site contained in the standard DNA (A), (B) and (C). Therefore, the four templates present in the mixed sample are amplified with the same efficiency. Specifically, the ratio among the four templates in the sample after PCR amplification is kept the same as that before amplification. To remove the dNTPs and PCR primers remaining in 400 μL of this PCR product, the PCR product was purified (500 μL) using QIAquick PCR Purification Kit. Each DNA concentration was measured using an absorption spectrometer to confirm that the concentrations were approximately 100 ng/μL. The sample was dissociated into single strands according to the Step 4. Then, luminescence attributed to single-base extension was measured according to the Step 5 to perform the quantitative analysis of the target DNA sample.

Example 4

Example 4 shows the quantitation of an expression level of EFF1G gene in human colon cancer cells (HCT116) by using a primer set with an anchor and reusing cDNA immobilized on magnetic beads as shown in Example 3.

First, cDNA immobilized on magnetic beads was used as a template for PCR amplification using primers with an anchor to add an anchor sequence to the target DNA. This target DNA sample with the added anchor sequence was collected into another tube. Subsequently, three standard DNAs (single-stranded) were prepared using a primer with an anchor having a substitution of only one base in the anchor sequence by another base species. The target DNA sample with the added anchor sequence prepared beforehand was mixed with these three standard DNAs in different amounts to perform PCR amplification. A PCR primer used in this amplification is designed to hybridize to the terminal side from the single-base substitution portion. Therefore, the target DNA sample and the standard DNAs can be amplified with the same application efficiency. This amplification product is dissociated into single strands, and the substituted base portion is extended by single-base extension. The complementary strand synthesis reaction occurs, during which pyrophosphoric acid is formed. This pyrophosphoric acid is converted to ATP, which in turn brings about detectable luminescence through a luciferase reaction. The obtained luminescence intensity is proportional to the amount of the pyrophosphoric acid. The type of the incorporated base species differs between the target and the standard samples. Therefore, the amount of each luminescence is measured separately. The target DNA is quantitated from the ratio of the measured amounts of luminescence and the amounts of the added standard DNA samples. In this case as well, only one standard DNA, not three, may be mixed with the target DNA sample for quantitative analysis.

Step 12: Preparation of Target Sequence Having Anchor Sequence Introduced Therein 10 μL of a single-stranded cDNA sample (cDNA derived from 100 pg of total RNA) was prepared using oligo(dT)$_{30}$-immobilized magnetic beads according to the Step 7. To 10 μL of the single-stranded cDNA sample, 39 μL of sterilized water, 10 μL of ×10 PCR Buffer, 10 μL of dNTP Mix (2.5 mM each), 20 μL of ×5 Q-solution, 10 μL of a forward primer G with an anchor (SEQ ID NO: 11) (10 μM), and 1 μL of Taq DNA polymerase (5 units/μL, QIAGEN) were added and mixed. This mixture was heated at 94° C. for 1 minute, 55° C. for 30 seconds, and 72° C. for 2 minutes for only one extension reaction using a thermal cycler. The reaction product was cooled on ice for approximately 1 minute. Then, the supernatant containing excessive primers, etc., unused in the reaction was removed by placing a magnet in proximity to the reaction tube. The magnetic beads were washed twice with 100 μL of a washing solution. Then, the magnetic beads were suspended in 10 μL of sterilized water heated to 95° C., and the supernatant was collected. This procedure was performed twice to obtain 20 μL of a target DNA sample with the anchor synthesized on the magnetic beads through heat denaturation.

Step 13: Preparation of Standard DNA Containing Anchor Sequence

A cDNA sample (cDNA derived from 10 pg of total RNA/μL) derived from colon cancer cells was obtained in the same way as in the Step 1. Three primers differing by only one base from the forward primer G with the anchor (SEQ ID NO: 11) used above, i.e., a forward primer H with an anchor (SEQ ID NO: 12), a forward primer I with an anchor (SEQ ID NO: 13), and a forward primer J with an anchor (SEQ ID NO: 14), were prepared. Three PCR tubes (tubes H, I, and J) were prepared on ice. To each of the tubes, 29 μL of sterilized water, 10 μL of ×10 PCR Buffer, 10 μL of dNTP Mix (2.5 mM each), 20 μL of ×5 Q-solution, 10 μL of a 5'-biotinylated reverse primer F (10 μM) (SEQ ID NO: 5), 1 μL of Taq DNA polymerase (5 units/μL, QIAGEN), and 10 μL of the target DNA sample were added. Further, 10 μL of the forward primer H (10 μM) was added to the tube H, 10 μL of the forward primer I (10 μM) was added to the tube I, and 10 μL of the forward primer J (10 μM) was added to the tube J. Each tube was well mixed. These mixtures were heated at 94° C. for 1 minute→50 cycles of 94° C. for 30 seconds, 58° C. for 30 seconds, and 72° C. for 1 minute→72° C. for 7 minutes for PCR amplification using a thermal cycler to obtain three double-stranded PCR products H, I, and J. Subsequently, to remove the dNTPs and PCR primers remaining in the sample, each PCR product was purified (50 μL) using QIAquick PCR Purification Kit (QIAGEN). Each DNA concentration was measured using an absorption spectrometer to confirm that all the concentrations were approximately 1 μg/μL.

These PCR products H, I, and J were separately diluted to 200 μL by the addition of 150 μL of 1× Binding & Washing Buffer (5 mM Tris-HCl (pH 7.5), 0.5 mM EDTA, 1 M NaCl). 600 μL of streptavidin-coated magnetic beads (1 μm in diameter, $10^7$ pieces/μL, DYNAL BIOTECH) was collected into a 1.5-mL tube and captured by placing a magnet in proximity to the tube, and the supernatant was removed. The magnetic beads were washed three times with 600 μL of Binding & Washing Buffer and then suspended in 600 μL of this buffer. A 200 μL aliquot of this magnetic bead suspension was added to each PCR product sample and well stirred for 60 minutes using a rotor (600 rpm, room temperature) to bind the PCR product onto the magnetic bead surface via the streptavidin-biotin bond. To remove excessive PCR products unbound with the magnetic beads, the magnetic beads were captured with a magnet, and the supernatant was removed. The beads were washed twice with 200 μL of Binding & Washing Buffer. Subsequently, the magnetic beads bound with each PCR product were suspended in 300 μL of 0.1 N NaOH and left standing at room temperature for 5 minutes. The magnetic beads were captured with a magnet, and each supernatant was collected into a new tube. To this supernatant, 60 μL of 1 M Tris (pH 7.5) and 300 μL of 0.1% Tween (pH 7.5) were added for neutralization. To each sample, 1 mL of phenol:chloroform:isoamyl alcohol (25:24:1, v/v, Invitrogen Corp.) was added. After vortex for 3 minutes, the mixture was centrifuged (15000 rpm, 5 minutes, room temperature) (phenol/chloroform purification). The upper layer of each centrifuged solution was collected (approximately 650 μL) into a new tube and purified and concentrated (approximately 250 μL) using QIAquick PCR Purification Kit. To these samples, 25 μL of sodium acetate (3 M) and 625 μL of ethanol (99.5%, −30° C.) were added, and the mixture was frozen at −80° C. for 15 minutes and then centrifuged (15000 rpm, 15 minutes, 4° C.). 180 μL of ethanol (70%, −30° C.) was added to each sample. The mixture was centrifuged (15000 rpm, 5 minutes, 4° C.), and the supernatant was removed (ethanol precipitation purification). Each pellet was dried and then suspended in 10 μL of sterilized water. Each DNA concentration was measured using an absorption spectrometer to confirm that all the concentrations were approximately 2 μg/μL (approximately $2 \times 10^{12}$ molecules/μL). These suspensions were diluted with sterilized water to prepare 1 mL each of approximately 1000 molecules/μL standard DNA (H) (SEQ ID NO: 15), approximately 500 molecules/μL standard DNA (I) (SEQ ID NO: 16), and approximately 100 molecules/μL standard DNA (J) (SEQ ID NO: 17). These standard DNAs are single-stranded DNAs differing by only one base from the target DNA.

Step 14: Mixing of Target DNA Sample with Standard DNA Sample and PCR Amplification To a tube placed on ice, 20 μL of the target DNA sample with the anchor prepared in the Step 12 and 10 μL each of the standard DNAs (H), (I), and (J) were added to prepare a mixed sample. This mixed sample was mixed with 106 μL of sterilized water, 40 μL of ×10 PCR Buffer, 40 μL of dNTP Mix (2.5 mM each), 80 μL of ×5 Q-solution, 40 μL of a forward primer K (SEQ ID NO: 18) (10 μM), 40 μL of a 5'-biotinylated reverse primer F (10 μM) (SEQ ID NO: 5), and 4 μL of Taq DNA polymerase (5 units/μL, QIAGEN). This mixture was heated at 94° C. for 1 minute→50 cycles of 94° C. for 30 seconds, 58° C. for 30 seconds, and 72° C. for 1 minute→72° C. for 7 minutes for PCR amplification using a thermal cycler.

The primer used in this PCR amplification is designed to hybridize to the terminal side from the single-base substitution site contained in the standard DNAs (H), (I), and (J). Therefore, the four DNAs with different substituted bases present in the mixed sample are amplified with the same efficiency. Specifically, the ratio among the four DNAs in the sample after PCR amplification is kept the same as that before amplification. To remove the dNTPs and PCR primers remaining in 400 μL of the PCR product, the PCR product was purified (500 μL) using QIAquick PCR Purification Kit. Each DNA concentration was measured using an absorption spectrometer to confirm that the concentrations were approximately 100 ng/μL. 100 μL of a single-stranded PCR product (approximately $5 \times 10^{11}$ molecules/μL) was obtained in the same way as in the Step 4.

Step 15: Measurement of Chemical Luminescence Attributed to Single-Base Extension 8 μl of the single-stranded PCR amplification product was mixed with 3 μL of a probe for single-base extension (50 μM, SEQ ID NO: 19) (405), 3 μl of 10× Hybridization Buffer (100 mM Tris-acetate, 20 mM Mg-Acetate, pH 7.75), and 16 μl of sterilized water. The mixed solution was heated at 92° C. for 30 seconds and 50° C. for 3 minutes using a thermal cycler and cooled to 4° C. A 4 μL aliquot of this solution was mixed with 120 μL of a luminescence reagent (0.065 U/μL Sequenase, 100 mM Tricine, 2 mM EDTA, 20 mM Mg-Acetate, 33.8 U/ml PPDK-E, 523.0 GLU/ml Luciferase (LUC-H), Apyrase 1.5 U/ml Grade VI, 0.4 mM Luciferin, 0.04 mM PEP, 0.2 mM AMP, 0.10% BSA, 2 mM DTT, pH 7.75) and incubated at 30° C. for 1 minute. A 30 μL aliquot thereof was dispensed to each of four connected tubes, to which 0.5 μL each of ddNTPs (100 μM each) whose PPi was degraded in advance with PPase was added to perform luminescence detection (measurement time: 1 minute). Next the same amounts of ddNTPs were added thereto to perform luminescence detection again (measurement time: 1 minute).

A luminescence intensity signal is defined as a value obtained by subtracting the background luminescence intensity obtained in the second measurement from the luminescence intensity obtained in the first measurement. The luminescence intensity signal thus obtained was measured on 1 μL ($2 \times 10^{10}$ molecules) each of the four standard DNAs mixed with 30 μL of the luminescence reagent. An extension intensity ratio was obtained from the ratio among the luminescence intensity signals of these four standard DNAs relative to the signal value derived from ddATP. The difference in the degree of extension among the types of base species was corrected by dividing the luminescence intensity signal values by these numeric values of the extension intensity ratio. The upper line of Table 1 shows the luminescence signal values before correction, and the lower line of Table 1 shows the luminescence signal values after correction.

The corrected signal values were used to initially prepare a calibration curve 601 shown in FIG. 6 from the mixed three standard DNAs (H), (I), and (J) for quantitating the number of molecules of the target DNA sample. The luminescence intensity signal values (after correction) are plotted in the abscissa of the graph, and the numbers of molecules of the standard DNAs before PCR amplification are plotted in the ordinate thereof. Next, the calibration curve 601 was used to obtain the number of molecules (15500) corresponding to the target DNA sample as shown in an arrow 602, from the luminescence intensity signal value (after correction) obtained from the target DNA sample. This value is almost equal to the known number of molecules (15000) of the target, demonstrating that quantitation with sufficient accuracy can be achieved.

The present invention is useful in all fields such as medical care, science, and foods, which require the quantitative analysis of nucleic acid samples.

Free Text for Sequence Listing

SEQ ID NO: 2—primer
SEQ ID NO: 3—primer
SEQ ID NO: 4—primer
SEQ ID NO: 5—primer
SEQ ID NO: 6—standard DNA (A)
SEQ ID NO: 7—standard DNA (B)
SEQ ID NO: 8—standard DNA (C)
SEQ ID NO: 9—primer
SEQ ID NO: 10—probe for extension
SEQ ID NO: 11—primer
SEQ ID NO: 12—primer
SEQ ID NO: 13—primer
SEQ ID NO: 14—primer
SEQ ID NO: 15—standard DNA (H)
SEQ ID NO: 16—standard DNA (I)
SEQ ID NO: 17—standard DNA (J)
SEQ ID NO: 18—primer
SEQ ID NO: 19—primer

What is claimed is:

1. A method for nucleic acid quantitation, comprising the following steps:
   a) preparing a plurality of standard DNA samples each having a single-base substitution in its sequence relative to a sequence in a target DNA sample by carrying out a polymerase chain reaction with the use of primers, at least one of which primers comprises a primer sequence having a single-base substituted relative to a sequence of the target DNA at the 3rd to 10th base position from the 3' end of the primer and having at least 16 or more bases in its sequence in the 5' direction from the substituted base, thereby producing the standard DNAs each having the same sequence as that of the target DNA, except each of the standard DNAs has a single-base substitution relative to the sequence of the target DNA, wherein the plurality of standard DNA samples differ in the substituted base;
   b) mixing the target DNA sample with a predetermined amount of the plurality of standard DNA samples, wherein the plurality of standard DNA samples differ in concentration;
   c) amplifying the mixed sample using a set of primers which are completely complementary to the target DNA and the plurality of DNA standards to thereby amplify a region comprising the single-base substitution site;
   d) dissociating the amplified sample into single strands, hybridizing thereto a probe capable of binding to a site immediately before the single-base substitution site, and sequentially adding ddATP, ddGTP, ddCTP, and ddTTP one by one to the hybridization product to perform a complementary strand synthesis reaction, wherein the probe has a sequence completely complementary to the site immediately before the single-base substitution site of the target DNA and the standard DNAs;
   e) detecting luciferase reaction-induced luminescence derived from pyrophosphoric acid formed through the complementary strand synthesis reaction; and
   f) quantitating the target DNA from the amount of the detected luminescence and the amount of the standard DNA sample.

2. The method according to claim 1, wherein at least one of the primers is biotinylated, and the method further comprises the step of purifying the amplification product using streptavidin-conjugated beads.

3. The method according to claim 1, wherein the target DNA sample is a cDNA sample.

4. The method according to claim 1, wherein step a) further comprises adding an anchor sequence to the target DNA prior to carrying out the polymerase chain reaction with the use of the primers, at least one of which comprises the same sequence as the anchor sequence, except for having a single-base substitution introduced.

5. The method according to claim 1, wherein both the target and standard DNAs are in a free form.

6. The method according to claim 1, wherein at least one of the target and standard DNAs is immobilized on a solid phase surface.

7. The method according to claim 1, wherein the target DNA sample is immobilized on magnetic beads.

* * * * *

```
                        SEQUENCE LISTING

<160> NUMBER OF SEQ ID NOS: 19

<210> SEQ ID NO 1
<211> LENGTH: 319
<212> TYPE: DNA
<213> ORGANISM: Homo sapiens

<400> SEQUENCE: 1
tgatggcaag agatgttcac ttgaagatct tgccctgatt gaaggctttg cccacatgct      60
ggaaggcccc ctcccaggaa aagtactctc gaaccagcgt ctgggtctcc tcgctgccag     120
gatccagttt ccgccatgtg tatgactcgt agtccacctg ccaatctgga ctcagcggaa     180
aggcaagctc ctggcctcgg aagacccaga ctccagaaat ggagctgcta ttgttggttc     240
caaaaaggat gacactggcg aaggcattct tcctcagctt gtccagtcgc tggaacattc     300
cagtgatgag attgcagct                                                  319

<210> SEQ ID NO 2
<211> LENGTH: 27
<212> TYPE: DNA
<213> ORGANISM: Artificial Sequence
<220> FEATURE:
<223> OTHER INFORMATION: primer; chemically synthesized

<400> SEQUENCE: 2
agctgcaatc tcatcactgg gatgttc                                          27

<210> SEQ ID NO 3
<211> LENGTH: 27
<212> TYPE: DNA
<213> ORGANISM: Artificial Sequence
<220> FEATURE:
<223> OTHER INFORMATION: primer; chemically synthesized

<400> SEQUENCE: 3
agctgcaatc tcatcactgg catgttc                                          27

<210> SEQ ID NO 4
<211> LENGTH: 27
<212> TYPE: DNA
<213> ORGANISM: Artificial Sequence
<220> FEATURE:
<223> OTHER INFORMATION: primer; chemically synthesized

<400> SEQUENCE: 4
agctgcaatc tcatcactgg tatgttc                                          27

<210> SEQ ID NO 5
<211> LENGTH: 20
<212> TYPE: DNA
```

<213> ORGANISM: Artificial Sequence
<220> FEATURE:
<223> OTHER INFORMATION: primer; chemically synthesized

<400> SEQUENCE: 5
aatctggact cagcggaaag                                               20

<210> SEQ ID NO 6
<211> LENGTH: 319
<212> TYPE: DNA
<213> ORGANISM: Artificial Sequence
<220> FEATURE:
<223> OTHER INFORMATION: standard DNA(A); chemically synthesized

<400> SEQUENCE: 6
tgatggcaag agatgttcac ttgaagatct tgccctgatt gaaggctttg cccacatgct    60
ggaaggcccc ctcccaggaa aagtactctc gaaccagcgt ctgggtctcc tcgctgccag   120
gatccagttt ccgccatgtg tatgactcgt agtccacctg ccaatctgga ctcagcggaa   180
aggcaagctc ctggcctcgg aagacccaga ctccagaaat ggagctgcta ttgttggttc   240
caaaaaggat gacactggcg aaggcattct tcctcagctt gtccagtcgc tggaacatcc   300
cagtgatgag attgcagct                                               319

<210> SEQ ID NO 7
<211> LENGTH: 319
<212> TYPE: DNA
<213> ORGANISM: Artificial Sequence
<220> FEATURE:
<223> OTHER INFORMATION: standard DNA(B); chemically synthesized

<400> SEQUENCE: 7
tgatggcaag agatgttcac ttgaagatct tgccctgatt gaaggctttg cccacatgct    60
ggaaggcccc ctcccaggaa aagtactctc gaaccagcgt ctgggtctcc tcgctgccag   120
gatccagttt ccgccatgtg tatgactcgt agtccacctg ccaatctgga ctcagcggaa   180
aggcaagctc ctggcctcgg aagacccaga ctccagaaat ggagctgcta ttgttggttc   240
caaaaaggat gacactggcg aaggcattct tcctcagctt gtccagtcgc tggaacatgc   300
cagtgatgag attgcagct                                               319

<210> SEQ ID NO 8
<211> LENGTH: 319
<212> TYPE: DNA
<213> ORGANISM: Artificial Sequence
<220> FEATURE:
<223> OTHER INFORMATION: standard DNA(C); chemically synthesized

<400> SEQUENCE: 8
tgatggcaag agatgttcac ttgaagatct tgccctgatt gaaggctttg cccacatgct    60
ggaaggcccc ctcccaggaa aagtactctc gaaccagcgt ctgggtctcc tcgctgccag   120
gatccagttt ccgccatgtg tatgactcgt agtccacctg ccaatctgga ctcagcggaa   180
aggcaagctc ctggcctcgg aagacccaga ctccagaaat ggagctgcta ttgttggttc   240
caaaaaggat gacactggcg aaggcattct tcctcagctt gtccagtcgc tggaacatac   300
cagtgatgag attgcagct                                               319

<210> SEQ ID NO 9
<211> LENGTH: 20
<212> TYPE: DNA
<213> ORGANISM: Artificial Sequence
<220> FEATURE:

<223> OTHER INFORMATION: primer; chemically synthesized

<400> SEQUENCE: 9
agctgcaatc tcatcactgg                                                    20

<210> SEQ ID NO 10
<211> LENGTH: 19
<212> TYPE: DNA
<213> ORGANISM: Artificial Sequence
<220> FEATURE:
<223> OTHER INFORMATION: extension probe; chemically synthesized

<400> SEQUENCE: 10
tgtccagtcg ctggaacat                                                     19

<210> SEQ ID NO 11
<211> LENGTH: 47
<212> TYPE: DNA
<213> ORGANISM: Artificial Sequence
<220> FEATURE:
<223> OTHER INFORMATION: primer; chemically synthesized

<400> SEQUENCE: 11
agcggataac aatttcacac aggaaacagc tgcaatctca tcactgg                      47

<210> SEQ ID NO 12
<211> LENGTH: 47
<212> TYPE: DNA
<213> ORGANISM: Artificial Sequence
<220> FEATURE:
<223> OTHER INFORMATION: primer; chemically synthesized

<400> SEQUENCE: 12
agcggataac aatttcacac agggaacagc tgcaatctca tcactgg                      47

<210> SEQ ID NO 13
<211> LENGTH: 47
<212> TYPE: DNA
<213> ORGANISM: Artificial Sequence
<220> FEATURE:
<223> OTHER INFORMATION: primer; chemically synthesized

<400> SEQUENCE: 13
agcggataac aatttcacac aggcaacagc tgcaatctca tcactgg                      47

<210> SEQ ID NO 14
<211> LENGTH: 47
<212> TYPE: DNA
<213> ORGANISM: Artificial Sequence
<220> FEATURE:
<223> OTHER INFORMATION: primer;chemically synthesized

<400> SEQUENCE: 14
agcggataac aatttcacac aggtaacagc tgcaatctca tcactgg                      47

<210> SEQ ID NO 15
<211> LENGTH: 346
<212> TYPE: DNA
<213> ORGANISM: Artificial Sequence
<220> FEATURE:
<223> OTHER INFORMATION: standard DNA(H); chemically synthesized

<400> SEQUENCE: 15
agcggataac aatttcacac aggaacagc tgcaatctca tcactggaat gttccagcga         60
ctggacaagc tgaggaagaa tgccttcgcc agtgtcatcc tttttggaac caacaatagc       120

-continued

| | |
|---|---|
| agctccattt ctggagtctg gtcttccga ggccaggagc ttgcctttcc gctgagtcca | 180 |
| gattggcagg tggactacga gtcatacaca tggcggaaac tggatcctgg cagcgaggag | 240 |
| acccagacgc tggttcgaga gtacttttcc tgggaggggg ccttccagca tgtgggcaaa | 300 |
| gccttcaatc agggcaagat cttcaagtga acatctcttg ccatca | 346 |

<210> SEQ ID NO 16
<211> LENGTH: 346
<212> TYPE: DNA
<213> ORGANISM: Artificial Sequence
<220> FEATURE:
<223> OTHER INFORMATION: standard DNA(I); chemically synthesized

<400> SEQUENCE: 16

| | |
|---|---|
| agcggataac aatttcacac aggcaacagc tgcaatctca tcactggaat gttccagcga | 60 |
| ctggacaagc tgaggaagaa tgccttcgcc agtgtcatcc tttttggaac caacaatagc | 120 |
| agctccattt ctggagtctg gtcttccga ggccaggagc ttgcctttcc gctgagtcca | 180 |
| gattggcagg tggactacga gtcatacaca tggcggaaac tggatcctgg cagcgaggag | 240 |
| acccagacgc tggttcgaga gtacttttcc tgggaggggg ccttccagca tgtgggcaaa | 300 |
| gccttcaatc agggcaagat cttcaagtga acatctcttg ccatca | 346 |

<210> SEQ ID NO 17
<211> LENGTH: 346
<212> TYPE: DNA
<213> ORGANISM: Artificial Sequence
<220> FEATURE:
<223> OTHER INFORMATION: standard DNA(J); chemically synthesized

<400> SEQUENCE: 17

| | |
|---|---|
| agcggataac aatttcacac aggtaacagc tgcaatctca tcactggaat gttccagcga | 60 |
| ctggacaagc tgaggaagaa tgccttcgcc agtgtcatcc tttttggaac caacaatagc | 120 |
| agctccattt ctggagtctg gtcttccga ggccaggagc ttgcctttcc gctgagtcca | 180 |
| gattggcagg tggactacga gtcatacaca tggcggaaac tggatcctgg cagcgaggag | 240 |
| acccagacgc tggttcgaga gtacttttcc tgggaggggg ccttccagca tgtgggcaaa | 300 |
| gccttcaatc agggcaagat cttcaagtga acatctcttg ccatca | 346 |

<210> SEQ ID NO 18
<211> LENGTH: 20
<212> TYPE: DNA
<213> ORGANISM: Artificial Sequence
<220> FEATURE:
<223> OTHER INFORMATION: primer; chemically synthesized

<400> SEQUENCE: 18

| | |
|---|---|
| agcggataac aatttcacac | 20 |

<210> SEQ ID NO 19
<211> LENGTH: 20
<212> TYPE: DNA
<213> ORGANISM: Artificial Sequence
<220> FEATURE:
<223> OTHER INFORMATION: primer; chemically synthesized

<400> SEQUENCE: 19

| | |
|---|---|
| gtgatgagat tgcagctgtt | 20 |